United States Patent [19]

Leimgruber et al.

[11] 3,937,707

[45] Feb. 10, 1976

[54] 6-SUBSTITUTED 1-PHENAZINOL 5,10-DIOXIDE DERIVATIVES

[75] Inventors: Willy Leimgruber, Montclair; Manfred Weigele, North Caldwell, both of N.J.

[73] Assignee: Hoffmann-La Roche Inc., Nutley, N.J.

[22] Filed: July 22, 1974

[21] Appl. No.: 490,615

Related U.S. Application Data

[60] Continuation of Ser. No. 248,907, May 1, 1972, Pat. No. 3,829,423, which is a division of Ser. No. 25,298, April 2, 1970, Pat. No. 3,681,331.

[52] U.S. Cl. ............................................. 260/267
[51] Int. Cl.$^2$ ..................................... C07D 241/46
[58] Field of Search .................................. 260/267

[56] References Cited
UNITED STATES PATENTS 3,586,674   6/1971   Leingruber et al. ................ 260/267

FOREIGN PATENTS OR APPLICATIONS 1,091,618   11/1967   United Kingdom ................ 260/267

OTHER PUBLICATIONS

Weigele et al. *Antimicrobial Agents Structurally Related to Myxin.* Antimicrobial Agents and Chemotherapy. 1971, pp. 46–49.

*Primary Examiner*—Richard J. Gallagher
*Assistant Examiner*—Anne Marie T. Tighe
*Attorney, Agent, or Firm*—Samuel L. Welt; Bernard S. Leon; Frank P. Hoffman

[57] ABSTRACT

6-Substituted derivatives of 1-phenazinol 5,10-dioxide which possess broad spectrum anti-microbial activity are disclosed.

3 Claims, No Drawings

6-SUBSTITUTED 1-PHENAZINOL 5,10-DIOXIDE DERIVATIVES

RELATED APPLICATIONS

This application is a continuation application of copending application Ser. No. 248,907 filed on May 1, 1972 now U.S. Pat. No. 3,829,423 issued Aug. 13, 1974 which in turn is a divisional application of copending application Ser. No. 25,298 filed Apr. 2, 1970 now U.S. Pat. No. 3,681,331 issued Aug. 1, 1972 in the names of Leimgruber and Weigele.

DESCRIPTION OF THE INVENTION

This invention relates to novel 6-substituted derivatives of 1-phenazinol 5,10-dioxide and to methods for their preparation. More particularly, the invention relates to derivatives of 1,6-phenazinediol 5,10-dioxide, the known antibiotic iodinin, which are prepared by monoalkylation of one of the two hydroxyl groups of the molecule. These novel derivatives exhibit broad spectrum anti-microbial activity and have the added advantage over the parent antibiotic of possessing better solubility properties.

The novel derivatives to which the invention relates are selected from the group consisting of compounds represented by the formula

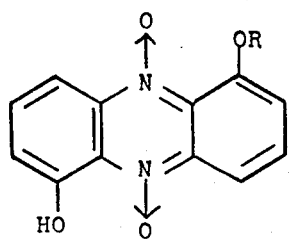

I wherein R is selected from the group consisting of alkyl containing from 4 to 10 carbon atoms, halo-lower alkyl, lower alkenyl, lower alkynyl, amino-lower alkyl, di-lower alkylamino-lower alkyl, phthalimido-N-lower alkyl and Z-lower alkyl wherein Z signifies a 5 or 6 membered saturated heterocyclic ring containing a nitrogen atom and at most one further hetero atom consisting of oxygen and in cases where R signifies amino-lower alkyl, di-lower alkylamino-lower alkyl and Z-lower alkyl, the pharmaceutically acceptable acid addition salts thereof.

As used herein, the term "alkyl" denotes straight or branched chain saturated hydrocarbon radicals containing from 4 to 10 carbon atoms inclusive, such as butyl, 3-methylbutyl, pentyl, hexyl, heptyl and the like. The term "lower alkyl" denotes straight or branched chain saturated hydrocarbon radicals containing from 1 to 7 carbon atoms inclusive, such as methyl, ethyl, propyl, isopropyl, butyl, pentyl, hexyl and the like, with groups containing from 1 to 4 carbon atoms being preferred. The term "lower alkenyl" denotes an unsaturated univalent aliphatic radical having at least one double bond and containing from 3 to 7 carbon atoms inclusive, with groups containing from 3 to 4 carbon atoms being preferred. The term "lower alkynyl" denotes an unsaturated univalent aliphatic radical having at least one triple bond and containing from 3 to 7 carbon atoms with groups containing from 3 to 4 carbon atoms being preferred. The term "halogen" includes fluorine, chlorine, bromine and iodine unless expressly indicated otherwise.

In a preferred aspect, when R signifies Z-lower alkyl, Z being defined as above, the heterocyclic ring is saturated and represents a member selected from the group consisting of morpholino, piperidino, and pyrrolidino.

Representative of the compounds of formula I are:
6-(3-methylbutoxy)-1-phenazinol 5,10-dioxide
6-heptyloxy-1-phenazinol 5,10-dioxide
6-decyloxy-1-phenazinol 5,10-dioxide
6-allyloxy-1-phenazinol 5,10-dioxide
6-(2-propynyloxy)-1-phenazinol 5,10-dioxide
6-(3-phthalimidopropoxy)-1-phenazinol 5,10-dioxide
6-(3-aminopropoxy)-1-phenazinol 5,10-dioxide
6-(3-chloropropoxy)-1-phenazinol 5,10-dioxide
6-(3-pyrrolidinopropoxy)-1-phenazinol 5,10-dioxide
6-(3-dimethylaminopropoxy)-1-phenazinol 5,10-dioxide
6-(3-piperidinopropoxy)-1-phenazinol 5,10-dioxide
6-(3-diethylaminopropoxy)-1-phenazinol 5,10-dioxide
6-(3-morpholinopropoxy)-1-phenazinol 5,10-dioxide A preferred class of compounds falling within the scope of formula I are those wherein R signifies alkyl containing from 4 to 10 carbon atoms, halo-lower alkyl, lower alkenyl or lower alkynyl, i.e., compounds of the formula

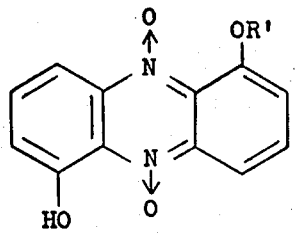

Ia wherein R' signifies alkyl containing from 4 to 10 carbon atoms, halo-lower alkyl, lower alkenyl or lower alkynyl.

The compounds of formula Ia are preferred because of their interesting level of activity.

Another class of compounds preferred because of their interesting level of activity falling within the scope of the present invention are those wherein R signifies amino-lower alkyl or dilower alkylamino-lower alkyl, i.e., compounds of the formula

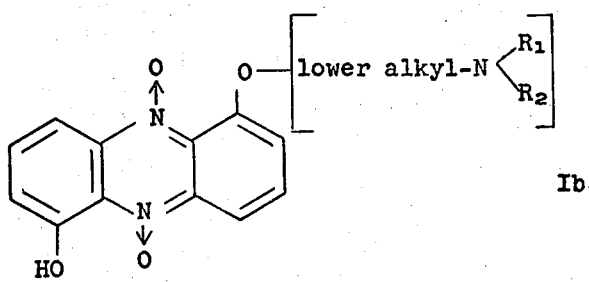

Ib wherein $R_1$ and $R_2$ are the same and are selected from the group consisting of hydrogen or lower alkyl and the pharmaceutically acceptable acid addition salts thereof.

Most preferred of the compounds of formula I are:
6-(3-methylbutoxy)-1-phenazinol 5,10-dioxide
6-heptyloxy-1-phenazinol 5,10-dioxide
6-allyloxy-1-phenazinol 5,10-dioxide
6-(2-propynyloxy)-1-phenazinol 5,10-dioxide
6-(3-aminopropoxy)-1-phenazinol 5,10-dioxide
6-(3-dimethylaminopropoxy)-1-phenazinol 5,10-dioxide
6-(3-diethylaminopropoxy)-1-phenazinol 5,10-dioxide
6-(3-pyrrolidinopropoxy)-1-phenazinol 5,10-dioxide
6-(3-morpholinopropoxy)-1-phenazinol 5,10-dioxide Also included within the scope of the present invention are the pharmaceutically acceptable acid addition salts of the compounds of formula I wherein R is amino-lower alkyl, di-lower alkylamino-lower alkyl or Z-lower alkyl, Z being defined as above. This class of compounds falling within the scope of formula I form pharmaceutically acceptable acid addition salts with pharmaceutically acceptable organic and inorganic acids such as hydrochloric acid, hydrobromic acid, sulfuric acid, phosphoric acid, nitric acid, tartaric acid, citric acid, salicylic acid, maleic acid, succinic acid, acetic acid and the like.

The compounds of formula I above may be prepared following a variety of procedures. The choice of procedure will depend upon the nature of the R substituent to be introduced into the phenazinol molecule.

For example, compounds of formula I wherein R signifies alkyl containing from 4 to 10 carbon atoms, halo-lower alkyl, lower alkenyl, lower alkynyl, or phthalimido-N-lower alkyl can be prepared using conventional alkylating techniques. This alkylating procedure is preferably carried out in two stages. In the first stage, the known compound 1,6-phenazinediol 5,10-dioxide (iodinin), which is used as the starting material, is converted to its mono-alkali metal salt, preferably the potassium salt. The conversion of iodinin to its alkali metal salt is accomplished by reacting iodinin with an alkali metal base. This reaction is expediently effected in the presence of an aprotic polar organic solvent, such as hexamethylphosphoric triamide (HMPT), dimethylformamide (DMF) or dimethylsulfoxide (DMSO), with HMPT being preferred. Use of an aprotic polar organic solvent is preferred since these solvents can also be utilized in the alkylation step, thus eliminating the necessity of first isolating the iodinin salt. Suitable alkali metal bases that may be used to form the iodinin salt include alkali metal lower alkoxides containing from 1 to 4 carbon atoms. Preferred alkali metal lower alkoxides include the sodium and potassium compounds, with potassium t-butoxide being the most preferred alkali metal lower alkoxide.

In the second stage of the alkylation process, the monoalkali metal salt of iodinin is selectively alkylated by reacting said salt with a conventional alkylating agent. Suitable alkylating agents for this purpose include alkyl halides, alkyl sulfates, lower alkenyl halides, lower alkynyl halides, halo-lower alkyl halides, and phthalimido-N-lower alkyl halides. The halide compounds are preferably utilized and the bromides are the preferred compounds. Examples of suitable preferred alkylating agents include 1-bromo-3-methyl-butane, 1-bromo-heptane, 1-bromo-decane, allyl-bromide, 1-bromo-2-propyne, 1-bromo-3-chloro-propane, 1-chloro-4-bromo-butane, and phthalimido-N-propyl bromide.

As indicated above, this selective alkylation of the monoalkali metal salt of iodinin is expediently effected in the presence of an aprotic polar organic solvent such as HMPT, DMF and DMSO, with HMPT being the preferred solvent. The alkylation reaction conditions can be varied. However, suitable conditions which are convenient and provide good yields include the use of temperatures between about 10°C and about 70°C and reaction times sufficient to complete the reaction, usually from about 1 to about 24 hours. In a preferred aspect, the alkylation reaction is effected at room temperature, i.e., about 20° to 25°C.

In a further process aspect of the present invention, the novel compounds of formula I wherein the R substituent is an amino-lower alkyl group can be prepared by the solvolytic cleavage of a compound of formula I wherein the R substituent signifies a phthalimido-N-lower alkyl group. The solvolytic cleavage of the phthalimido derivative yields the desired amino compound. This solvolysis is effected by treating the phthalimido derivative with a conventional solvolyzing agent such as monomethylamine. Further, this reaction is expediently effected in the presence of an inert organic solvent. Suitable solvents for this purpose include alcohols such as methanol, ethanol and the like. The solvolysis reaction conditions may be varied. However, suitable conditions which are convenient and provide good yields include the use of temperatures in the range of from about 10°C to about 70°C, with room temperature being preferred, and reaction times sufficient to complete the reaction, usually from about 1 to about 10 hours.

In a further process aspect of the present invention, the novel compounds of formula I wherein the R substituent signifies di-lower alkylamino-lower alkyl or Z-lower alkyl, wherein Z is as described above, can be prepared by reacting a compound of formula I wherein R signifies halo-lower alkyl with the corresponding amine. Representative amines that may be used in this reaction include dimethylamine, diethylamine, morpholine, piperidine, pyrrolidine and the like. This reaction is expediently effected by dissolving the halo-lower alkyl compound in an excess of the amine or in the presence of an aprotic polar organic solvent such as DMSO. Temperature and reaction time are not critical to this process aspect. Thus, temperatures between about 10°C and about 70°C are suitable, with room temperature being preferred.

The novel compounds of formula I have been found to possess broad spectrum anti-microbial activity. In particular, these compounds have demonstrated a high level of activity against a wide variety of bacteria, yeast and fungi such as *Streptococcus agalactiae*, *Staphylococcus aureus*, *Escherichia coli*, *Cornyebacterium pyogenes*, *Moraxella bovis*, *Pseudomonas aeruginosa*, *Candida albicans*, and *Microsporum canis*. The novel compounds of this invention are particularly useful in the treatment of animal diseases of microbial origin. When the novel compounds of formula I are employed in the treatment of microbial infections, they are conveniently utilized in combination with suitable pharmaceutical carrier materials. These compositions are formulated by uniformly distributing the compound of formula I throughout a vehicle that is chemically compatable with the particular compound, non-inhibiting with respect to the active ingredient, and essentially non-injurious to the body tissue under the conditions of use. When formulated into compositions suitable for topical administration, the novel compounds of this invention are preferably employed in amounts ranging from about 0.05 percent to about 1.0 percent by weight of the composition. The compounds of this invention, when employed in forms suitable for topical administration, may be utilized in varied formulations: for example, in solid formulations including finely divided powders and granular materials, in liquid formulations including solutions, suspensions, concentrations, tinctures, slurries, aerosols and the like. Further, they may be employed as creams, gels, jellies, ointments, pastes, etc.

The following examples further illustrate the scope of the invention. All temperatures given are in degrees centigrade unless indicated otherwise.

EXAMPLE 1

Preparation of 6-(3-methylbutoxy)-1-phenazinol 5,10-dioxide 2.44 grams of iodinin were suspended in 150ml of hexamethylphosphoric triamide (HMPT) and 1.3 g of potassium t-butoxide were added with stirring. The reaction mixture was stirred overnight and then 10ml of 1-bromo-3-methyl-butane were added. Stirring continued at room temperature for 24 hours. The reaction mixture was then poured into ice water and extracted three times with ethyl acetate. The extracts were diluted with benzene, washed with water, dried over magnesium sulfate and evaporated to dryness in vacuo. The residue was chromatographed on silica gel with methylene chloride/ethyl acetate. Fractions containing the desired product were combined and evaporated in vacuo. The material was recrystallized from dichloromethane/acetone to yield 6-(3-methylbutoxy)-1-phenazinol 5,10-dioxide, m.p. 121° (dec.).

EXAMPLE 2

Preparation of 6-heptyloxy-1-phenazinol 5,10-dioxide 2.44 grams of iodinin were suspended in 150ml of HMPT. Then 1.3 grams of potassium t-butoxide were added with stirring. Stirring was continued over night. then 10ml of n-bromo-heptane were added and the stirring was continued at room temperature for 24 hours. The reaction mixture was poured into ice water and extracted with ethyl acetate. Extracts were diluted with benzene, washed with water, dried over magnesium sulfate and evaporated to dryness. The residue was redissolved in 200ml of $CH_2Cl_2$ and applied to a chromatography column containing 250 g silica gel. The material was eluted with methylene chloride/ethyl acetate. Fractions containing the desired product were combined and evaporated in vacuo. The material was recrystallized from dichloromethane/ acetone to yield 6-heptyloxy-1-phenazinol 5,10-dioxide, m.p. 91°–93° (dec.).

EXAMPLE 3

Preparation of 6-decyloxy-1-phenazinol 5,10-dioxide 2.44 grams of iodinin were suspended in 150ml HMPT. To this 1.3 grams of potassium t-butoxide were added with stirring. The stirring was continued overnight and then 10ml of 1-bromo-decane were added and the stirring continued at room temperature for 24 hours. The reaction mixture was poured into ice water and extracted three times with ethyl acetate. The extracts were diluted with benzene, washed with water, dried over magnesium sulfate and evaporated to dryness. The residue was chromatographed on silica gel with methylene chloride/ethyl acetate. Fractions containing the desired product were combined and evaporated in vacuo. The material was recrystallized from dichloromethane/acetone to yield 6-decyloxy-1-phenazinol 5,10-dioxide, m.p. 92°–95°(dec.).

EXAMPLE 4

Preparation of 6-allyloxy-1-phenazinol 5,10-dioxide 2.44 grams of iodinin were suspended in 150ml of HMPT. To this was added with stirring 1.3 grams of potassium t-butoxide. The reaction mixture was stirred overnight and 2.5 ml of allyl bromide were then added and the stirring continued at room temperature for 5 hours. The reaction mixture was then poured into ice water and extracted three times with ethyl acetate. Extracts were diluted with benzene, washed with water, dried over magnesium sulfate and evaporated to dryness. The residue was chromatographed on silica gel with methylene chloride/ethyl acetate. Fractions containing the desired product were combined and evaporated in vacuo. The material was recrystallized from dichloromethane/acetone to yield 6-allyloxy-1-phenazinol 5,10-dioxide, m.p. 142°(dec.).

EXAMPLE 5

Preparation of 6-(2-propynyloxy)-1-phenazinol 5,10-dioxide 2.44 grams of iodinin were suspended in 150ml HMPT. To this was added with stirring 1.3 grams of potassium t-butoxide. The reaction mixture was stirred overnight and then 2ml of 3-bromopropyne were added and stirring was continued at room temperature for 9 hours. The reaction mixture was then poured into ice water and extracted three times with ethyl acetate. The extracts were diluted with benzene, washed with water, dried over magnesium sulfate and evaporated in vacuo. The residue was chromatographed on 250 grams silica gel with $CHCl_3$/ethyl acetate. Fractions containing the desired product were combined and evaporated in vacuo. The material was recrystallized from di-chloro methane/acetone to yield 6-(2-propynyloxy)-1-phenazinol 5,10-dioxide, m.p. 152° (dec.).

EXAMPLE 6

Preparation of 1-(3-phthalimidopropoxy)-1-phenazinol 5,10-dioxide 7.32 grams of iodinin, 450ml HMPT and 3.9 grams of potassium tertiary butyl alcoholate were placed in a flask and stirred at room temperature overnight. To this was added 15 grams of N-(3-bromopropyl)phthalimide and stirring was continued for 17 hours. The reaction mixture was then poured into 4 liters of ice water and allowed to stand for 30 minutes. The precipitated solids were filtered and washed with 2 × 1 liter of water. The product was then washed with 300 ml of methanol and air dried to yield 1-(3-phthalimidopropoxy)-1-phenazinol 5,10-dioxide as a red powder, m.p. 161° (dec.).

EXAMPLE 7

Preparation of 6-(3-aminopropoxy)-1-phenazinol 5,10-dioxide hydrochloride 5 grams of 1-(3-phthalimidopropoxy)-1-phenazinol 5,10-dioxide were dissolved in 1000 ml of ethanol containing 100 grams of monomethylamine. The solution was stirred at room temperature for 4½ hours. It was then concentrated to approximately half the volume, and then diluted with 1500 ml of water and extracted with 4 × 1000 ml of chloroform. The combined extracts were extracted with 4 × 150 ml of 10 percent hydrochloric acid. The acidic solution was made alkaline with anhydrous sodium carbonate and this was extracted with 4 × 1000 ml of chloroform. The chloroform extracts were dried over sodium sulfate and evaporated in vacuo. The residue was redissolved in chloroform and the chloroform solution was shaken with approximately 15 percent aqueous HCl. The hydrochloride salt precipitated and was collected by filtration. The filter cake was washed with acetone and dried to yield 6-(3-aminopropoxy)-1-phenazinol 5,10-dioxide hydrochloride, m.p. 137°–138° (dec.).

EXAMPLE 8

Preparation of 6-(3-chloropropoxy)-1-phenazinol, 5,10-dioxide 7.32 grams of iodinin were suspended in 450 ml of HMPT. To this was added with stirring at room temperature 3.9 grams of potassium tertiary butyl alcoholate. Stirring was continued overnight. 18 ml of 1-bromo-3-chloropropane were added and stirring was continued at room temperature for 24 hours. The reaction mixture was then poured into 3500 ml of ice water. The precipitate was filtered off, washed with water and 15 ml of acetone. The filter cake was dried in vacuo and purified by chromatography on 500 grams of silica gel with dichloromethane/ethyl acetate. Fractions containing the desired product were combined and evaporated in vacuo to yield 6-(3-chloropropoxy)-1-phenazinol 5,10-dioxide, m.p. 137°(dec.).

EXAMPLE 9

Preparation of 6-(3-dimethylaminopropoxy)-1-phenazinol 5,10-dioxide

Into a sealed tube was placed 2.0 grams of 6-(3-chloropropoxy)-1-phenazinol 5,10-dioxide. The tube was cooled in dry-ice-acetone and 80 ml of dimethylamine was condensed into the tube. The tube was sealed and shaken at room temperature for 70 hours. The tube was then opened and excess dimethylamine allowed to evaporate at room temperature. The residue was dissolved in $CHCl_3$ solution, was washed with water and was then extracted with 3 × 150ml 10 percent aqueous HCl. The combined acid extracts were made basic with sodium carbonate, extracted with $CHCl_3$ and the combined $CHCl_3$ extracts were washed with water, dried over sodium sulfate and concentrated in vacuo. The residue was recrystallized from acetone/ether to yield 6-(3-dimethylaminopropoxy)-1-phenazinol 5,10-dioxide, mp. 103°C (dec.).

EXAMPLE 10

Preparation of 6-(3-diethylaminopropoxy)-1-phenazinol 5,10-dioxide 5.0 grams of 6-(3-chloropropoxy)-1-phenazinol 5,10-dioxide and 25ml of diethylamine were placed in a flask. To this was added 50ml of dimethylsulfoxide. The reaction mixture was stirred at room temperature for 22 hours. The reaction mixture was then diluted with 400ml $CHCl_3$ and washed first with very dilute acetic acid and then with water until the water washes were neutral. The $CHCl_3$ layer was extracted with 10 percent aqueous HCl. The combined HCl extracts were neutralized with sodium carbonate and extracted with ethyl acetate. The combined ethyl acetate extracts were washed with water, dried over sodium sulfate and concentrated in vacuo. The residue was slurried with ether/pentane (1:1) and filtered to yield red crystals of 6-(3-diethylaminopropoxy)-1-phenazinol 5,10-dioxide, m.p. 78°–80° (dec.).

EXAMPLE 11

Preparation of 6-(3-pyrrolidinopropoxy)-1-phenazinol 5,10-dioxide 2.0 grams of 6-(3-chloropropoxy)-1-phenazinol 5,10-dioxide and 20ml of pyrrolidine were placed in a flask and stirred at room temperature for 3 ½ hours. The reaction mixture was diluted with $CHCl_3$ and washed repeatedly with water until the water washes were neutral. The chloroform solution was extracted with 3 × 150 ml of 10 percent aqueous HCl. The acid extracts were combined, neutralized with sodium carbonate, extracted with $CHCl_3$ and the combined $CHCl_3$ extracts were washed with water and dried over sodium sulfate and concentrated in vacuo. The residue was recrystallized from acetone. The solids were filtered and washed with a little ether and dried in vacuo at 50° for 16 hours to yield metallic red crystals of 6-(3-pyrrolidinopropoxy)-1-phenazinol 5,10-dioxide, m.p. 113°–114°C (dec.).

EXAMPLE 12

Preparation of 6-(3-morpholinopropoxy)-1-phenazinol 5,10-dioxide 1.0 gram of 6-(3-morpholinopropoxy)-1-phenazinol 5,10-dioxide and 10 ml of morpholine were placed in a flask and stirred at room temperature for 23 hours. The reaction mixture was diluted with water and extracted with $CHCl_3$ several times. The $CHCl_3$ extracts were combined and washed repeatedly with water until neutral. The organic layer was extracted with 10 percent aqueous HCl several times. The acid extracts were combined, were made basic with sodium carbonate and extracted with $CHCl_3$ several times. The combined $CHCl_3$ extracts were washed with water, dried over sodium sulfate and concentrated in vacuo. The residue was recrystallized from acetone to yield 6-(3-morpholinopropoxy)-1-phenazinol 5,10-dioxide, m.p. 135°C (dec.).

EXAMPLE 13

Preparation of 6-(3-piperidinopropoxy)-1-phenazinol 5,10-dioxide 6 grams of 6-(3-chloropropoxy)-1-phenazinol 5,10-dioxide and 40ml piperidine were placed in a flask and stirred at room remperature for 21 hours. The reaction mixture was diluted with 500ml of chloroform. The mixture was then washed with water until the aqueous washes were neutral, extracted with 3 × 250ml of 10 percent HCl. Combined acid extracts were neutralized with sodium carbonate and extracted with 4 × 500ml of chloroform. The chloroform extracts were washed with water, dried over sodium sulfate and evaporated in vacuo. The residue was recrystallized from acetone and dried for 16 hours at 50°C to yield 6-(3-piperidinopropoxy)-1-phenazinol 5,10-dioxide, m.p. 92°–97°C (dec.).

We claim:
1. A compound of the formula

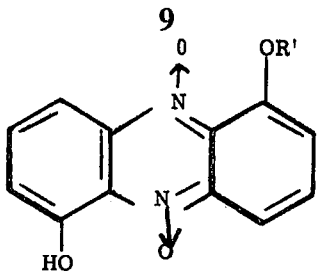
wherein R' is selected from the group consisting of halo-lower alkyl, and phthalimido-N-lower alkyl.
2. A compound of claim 1 of the formula 6-(3-chloropropoxy)-1-phenazinol 5,10-dioxide.
3. A compound of claim 1 of the formula 6-(3-phthalimidopropoxy)-1-phenazinol 5,10-dioxide.
* * * * *